(12) United States Patent
Kanazawa et al.

(10) Patent No.: US 7,549,751 B2
(45) Date of Patent: Jun. 23, 2009

(54) OPTOTYPE PRESENTING APPARATUS

(75) Inventors: Yuichiro Kanazawa, Okazaki (JP); Ryoji Suzuki, Toyohashi (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 12/010,975

(22) Filed: Jan. 31, 2008

(65) Prior Publication Data

US 2008/0204662 A1    Aug. 28, 2008

(30) Foreign Application Priority Data

Feb. 26, 2007    (JP)    .............................. 2007-045564

(51) Int. Cl.
*A61B 3/02* (2006.01)
(52) U.S. Cl. .................. 351/243; 351/237; 351/242
(58) Field of Classification Search .................. 351/200, 351/211, 222, 227, 237, 239, 242–246
See application file for complete search history.

(56) References Cited

U.S. PATENT DOCUMENTS

| | | | |
|---|---|---|---|
| 5,078,486 A | | 1/1992 | Evans |
| 5,568,209 A | | 10/1996 | Priester et al. |
| 5,880,814 A | | 3/1999 | McKnight et al. |
| 5,929,972 A | * | 7/1999 | Hutchinson .................. 351/237 |
| 6,425,665 B2 | | 7/2002 | Hayashi et al. |

FOREIGN PATENT DOCUMENTS

| | | |
|---|---|---|
| JP | A-2006-042978 | 2/2006 |
| WO | WO 02/076301 A1 | 10/2002 |

\* cited by examiner

*Primary Examiner*—William C Choi
*Assistant Examiner*—Jack Dinh
(74) *Attorney, Agent, or Firm*—Oliff & Berridge, PLC

(57) ABSTRACT

An optotype presenting apparatus which presents an optotype for visual acuity test, the apparatus comprises: a display that is illuminated by a backlight and includes a light intensity changing device which changes backlight intensity; a background luminance selecting device which selects background luminance of the optotype among a plurality of preset levels, in which background luminance at each level corresponds to standard light intensity changing data in a changeable range determined by the light intensity changing device; and a correction device which corrects the standard light intensity changing data in the background luminance selecting device, the correction device including: an input device which inputs the background luminance measured by an illuminance meter, the measured background luminance being background luminance obtained when the light intensity changing device is operated based on the preset light intensity changing data; and a calculation device which determines correction light intensity changing data by comparing the background luminance input by the input device and the preset light intensity changing data.

7 Claims, 7 Drawing Sheets

OPTOTYPE PRESENTING APPARATUS

BACKGROUND OF THE INVENTION

1. Field of the Invention

The present invention relates to an optotype presenting apparatus for examining visual acuity and others of an examinee's eye (a patient's eye) by presenting optotypes or charts.

2. Description of Related Art

As an optotype presenting apparatus for presenting optotypes or charts for visual acuity test, various types of apparatus have been known such as a display type apparatus arranged to display test optotypes or charts on a liquid crystal display or the like (e.g. see JP2006-42978A) as well as an apparatus arranged to present optotypes or charts printed on paper or the like by illuminating them with fluorescent light and an apparatus arranged to project optotypes or charts on a screen. In the display type apparatus, test optotypes or charts appear in black on a white background of the display illuminated by backlight.

In the case where the background luminance (illuminance) of optotypes largely varies from apparatus to apparatus, such variations may influence visual acuity test results. High background luminance tends to induce a good visual acuity test result as compared with low background luminance. Accordingly, apparatus manufacturers previously adjust and fix the background luminance in a relatively narrow range allowing the luminance to appear to be almost the same. However, the manufacturers around the world offer various optotype presenting apparatuses with different background luminances of test optotypes. Under present circumstances, the range of luminance permissible in visual acuity testing apparatuses (hereinafter, a "standard range") is considerably wide (80 to 320 cd/m$^2$, at present). In an optician's shop or an ophthalmological clinic, when an optotype presenting apparatus offered by a different manufacturer from a manufacturer of an existing apparatus used heretofore is additionally adopted, the new apparatus may have very different background luminance from that of the existing apparatus. In this case, those apparatuses could not have compatibility with each other.

To avoid such a disadvantage, it is conceivable that the display type optotype presenting apparatus is additionally provided with a function for changing the background luminance of optotypes by adjusting backlight intensity (level) of the display in a similar way to a computer display. This luminance change is performed by changing voltage to be applied to the backlight.

It was however found that the backlight intensity of the display largely varied among apparatuses even by the same adjustment value of applied voltage. Accordingly, if an adjustment value for changing the backlight intensity is uniformly set among the apparatuses, the background luminance of some of the apparatuses may fall outside the standard range permissible for the visual acuity test, resulting in lowered reliability of the visual acuity test. In the case where a plurality of optotype presenting apparatuses is newly adopted in the same place (the same shop or clinic), it is hard to adjust the background luminances of those apparatuses to the same luminance level to provide compatibility.

BRIEF SUMMARY OF THE INVENTION

The present invention has an object to provide an optotype presenting apparatus enabling an appropriate visual acuity test by changing background luminance of optotypes without falling outside a standard range permissible for the test, and further enabling easy adjustment of luminance even where a plurality of apparatuses is adjusted to have almost the same luminance.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optotype presenting apparatus which presents an optotype for visual acuity test, the apparatus comprising: a display that is illuminated by a backlight and includes a light intensity changing device which changes backlight intensity; a background luminance selecting device which selects background luminance of the optotype among a plurality of preset levels, in which background luminance at each level corresponds to standard light intensity changing data in a changeable range determined by the light intensity changing device; and a correction device which corrects the standard light intensity changing data in the background luminance selecting device, the correction device including: an input device which inputs the background luminance measured by an illuminance meter, the measured background luminance being background luminance obtained when the light intensity changing device is operated based on the preset light intensity changing data; and a calculation device which determines correction light intensity changing data by comparing the background luminance input by the input device and the preset light intensity changing data.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
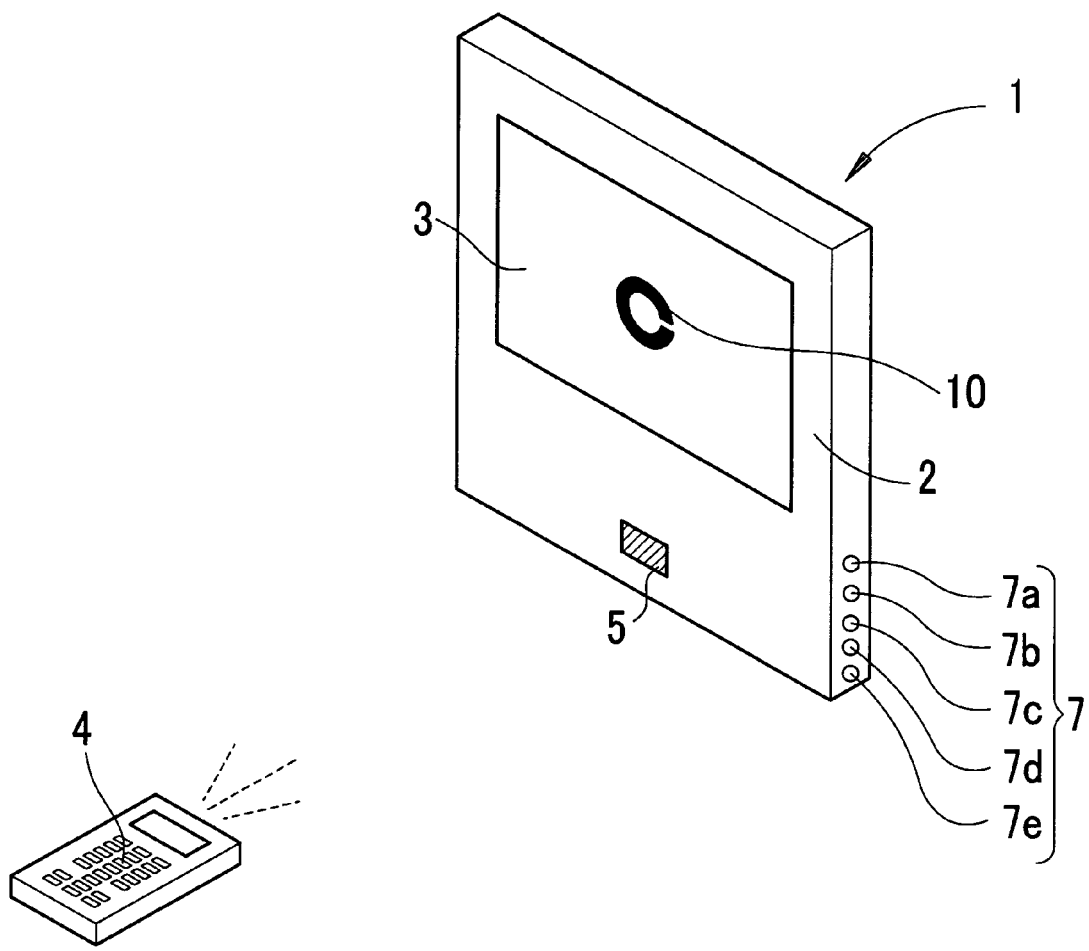
FIG. 1 is an external view of an optotype presenting apparatus of an embodiment.

A detailed description of a preferred embodiment of the present invention will now be given referring to the accompanying drawings. FIG. 1 is an external view of an optotype presenting apparatus of the present embodiment.

In a front surface of a housing 2 of an optotype presenting apparatus 1, a color liquid crystal display (LCD) 3 is arranged to present optotypes or charts. The display 3 used in the present embodiment is a 19-inch diagonal display in order to display a test optotype 10 of a predetermined size even where the apparatus is located at a far-vision test distance of 5 m, for example.

In a lower part of the front surface of the housing 2, a receiving part 5 is provided to receive infrared light communication signals from a remote control 4. On a right surface of the housing 2, a switch section 7 is provided including a plurality of switches 7a to 7e which are used for various settings of the apparatus in use. The optotype 10 displayed on the display 3 is changed to another by manipulation of the remote control 4. In the case of a visual acuity test optotype of a single character such as the optotype 10, the optotype 10 is displayed in almost the center of the display 3.

Figure 2:
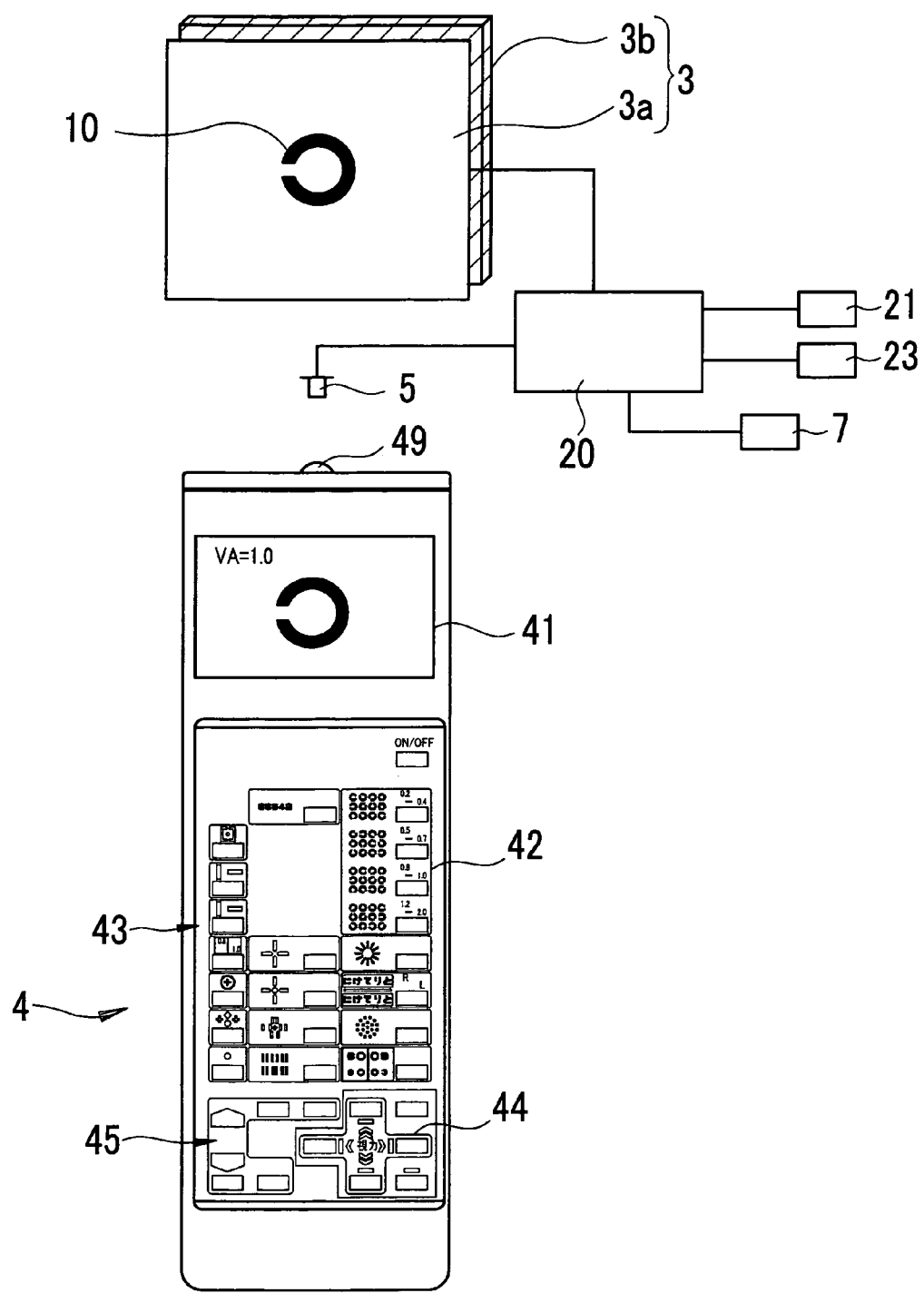
FIG. 2 is a diagram showing a control system of the optotype presenting apparatus.

FIG. 2 is a block diagram showing a control system of the optotype presenting apparatus 1. A control unit 20 is connected to the display 3, the receiving part 5, and a memory 21 which stores various optotype patterns, luminance adjustment values (the details thereof will be mentioned later), and others. The display 3 includes a liquid crystal panel 3a and a backlight 3b for illuminating the liquid crystal panel 3a from behind. The control unit 20 controls the backlight 3b to change the background luminance of the optotype 10 displayed on the liquid crystal panel 3a. The control unit 20 includes a circuit for controlling voltage for operating the backlight 3b. Further, the control unit 20 internally contains a decoder circuit for decoding command signals from the remote control 4 and others.

The remote control 4 is provided with a plurality of buttons for operating an apparatus main body and a liquid crystal display 41 which displays the operating condition set with those buttons. When one of visual acuity test optotype selector switches 42 corresponding to a visual acuity is selectively pressed, the optotype corresponding to the visual acuity is displayed on the display 3. Simultaneously, the same optotype appears together with the visual acuity on the display 41. Test optotype selector switches 43 are used to display various optotypes or charts for examining visual functions in a red-green test, a cross-cylinder test, a binocular vision test, etc. With press of an orientation-changing button 44, the orientation of a currently appearing optotype is changed to another one. With press of a visual acuity changing button 45, the visual acuity of the currently appearing optotype is increased or decreased. A transmitting part 49 is arranged to transmit a command signal from the remote control 4.

Meanwhile, the background luminance of the optotype 10 displayed on the display 3 has to fall within the range permissible for a visual acuity test (hereinafter, referred to as a "standard range"). This standard range is for example 80 cd/m$^2$ to 320 cd/m$^2$. However, this is a relatively wide permissible range. Even within this standard range, therefore, if the luminance largely varies among apparatuses, it may cause different visual acuity test results. To avoid such a disadvantage, during manufacture, the apparatus of the present embodiment is previously adjusted to have a substantially fixed luminance within a range (e.g., a range of ±20 cd/m$^2$ relative to a certain luminance) narrower than the standard range.

Furthermore, when an optotype presenting apparatus is newly adopted in addition to an existing optotype presenting apparatus used heretofore in a real optician's shop, the background luminance of the new apparatus may different from the existing apparatus. If the background luminance of the new apparatus is fixed, the new apparatus could not ensure compatibility with the existing apparatus. The apparatus of the present embodiment is therefore provided with a luminance changing function of changing the background luminance of optotypes or charts in two levels or more by changing an adjustment value (standard light intensity changing data) for changing the intensity of the backlight 3b of the display 3. The luminance change in the present embodiment is performed in five levels but may be conducted in more than five levels.

The intensity of the backlight 3b is changed by applied voltage output via a D/A converter and the like of the control unit 20. Specifically, when the voltage to be applied to the backlight 3b is changed in a range of for example 0V to 5V, the luminance becomes highest at 0V and lowest at 5V. The luminance adjustment value is expressed by 0 to 255 corresponding to the applied voltage of 0V to 5V divided into 256 scales so that 0V corresponds to an adjustment value "0" and 5V corresponds to an adjustment value "255". Accordingly, the control unit 20 controls to change the intensity of the backlight 3b according to the adjustment value, 0 to 255.

Figure 3:
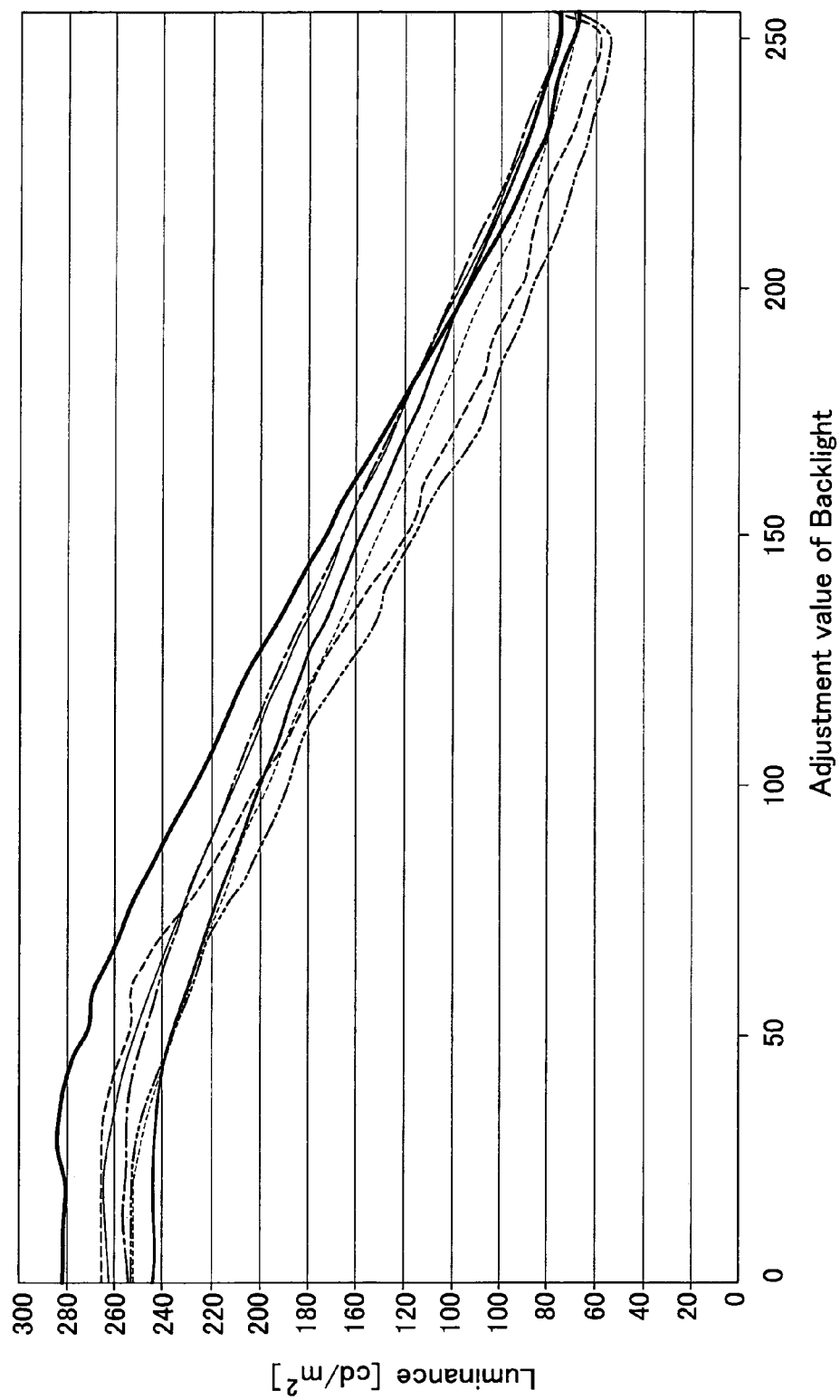
FIG. 3 is a graph showing a relationship between adjustment value and luminance.

Here, many optotype presenting apparatuses were manufactured and respective luminances were measured with a luminance meter by changing the adjustment value in a range of 0 to 255 in each apparatus. The results are shown in FIG. 3. As luminance measurement conditions, the luminances of a white background at five points around the optotype 10 (the center, above, below, the right, and the left of the optotype 10) were measured at a distance of 1 m and an average thereof was calculated.

Comparing relationships between luminance and adjustment value of the backlight 3b in the apparatuses, the luminance varies among the apparatuses even at the same adjustment value. The relationship is not partly proportional as viewed as a whole. In a range of 80 to 250 cd/m$^2$, however, the luminance of each apparatus changes in an almost proportional relationship with the backlight adjustment value. The maximum luminance and the minimum luminance are also different from apparatus to apparatus, but the inclinations of luminance change with respect to adjustment value are similar to one another. A rate of change to an adjustment value "10" is averagely about 10 cd/m$^2$. The minimum luminances are different in a range of 66 to 80 cd/m$^2$ and most of them are lower than 80 cd/m$^2$ which is a lower limit of the standard range. On the other hand, the maximum luminances are different in a range of 244 to 281 cd/m$^2$. All of the displays 3 used in the apparatuses did not provide the luminance exceeding 320 cd/m$^2$ which was an upper limit of the standard range. However, a display providing a luminance of more than 320 cd/m$^2$ is sufficiently likely to be created by recent improvements in high-luminance LCDs. When the luminance is changed in a simple manner using the same adjustment value of 0 to 255 among all the apparatuses, some of the apparatuses may provide the luminance outside the standard range (80 to 320 cd/m$^2$).

Consequently, the adjustment values previously set in correspondence to change levels are stored in the memory 21 so that the luminance falls within a predetermined permissible range at each change level without falling outside the standard range permissible for the visual acuity test even when the luminance is changed. The adjustment values (correction light intensity changing data) stored in the memory 21 are specific to each apparatus. The following explanation is given to a setting manner of the adjustment value.

Figure 4:
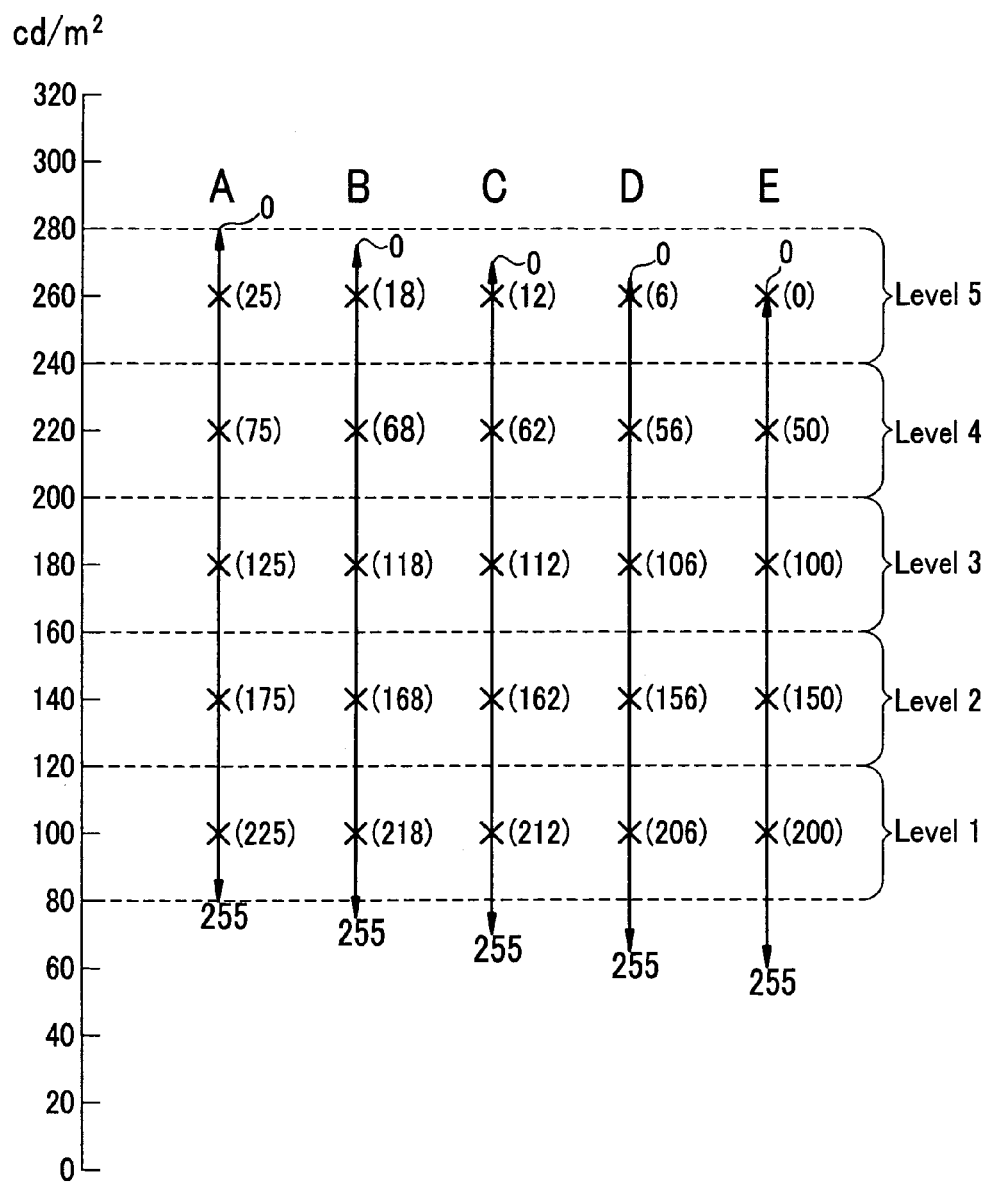
FIG. 4 is a chart to explain luminance change.

It is assumed that the apparatuses A to E shown in FIG. 4 have the following luminance ranges in relation to the adjustment values 0 to 255.

| | |
|---|---|
| A: | 80 to 280 cd/m$^2$ |
| B: | 75 to 275 cd/m$^2$ |
| C: | 70 to 270 cd/m$^2$ |

-continued

D:  65 to 265 cd/m²
E:  60 to 260 cd/m²

The five change levels are defined as Level 1 to Level 5, each of which is within the standard range. Level 1 is a minimum level close to 80 cd/m² which is the lower limit of the standard range but is not less than this lower limit. For example, Level 1 is set to be 100±20 cd/m². Level 5 is a maximum level, at which the luminance is set to be 200 cd/m² or more and within the standard range permissible for visual acuity test optotypes. In the present embodiment, based on the experimental results shown in FIG. 3, Level 5 is set to 260±20 cd/m² in view of the performance of the backlight 3b of the display 3. Between the minimum level, Level 1, and the maximum level, Level 5, middle levels are defined by predetermined ranges (±20 cd/m² in the present embodiment) in each of which luminance appears to be almost the same. For instance, Level 2 is set to be 140±20 cd/m², Level 3 is set to be 180±20 cd/m², and Level 4 is set to be 220±20 cd/m².

In each of the above apparatuses, it was confirmed that the maximum luminance of the display was 320 cd/m² or lower; specifically, in a range of 244 to 281 cd/m². Accordingly, Level 5 is set as the maximum level in the present embodiment. If the luminance of the display 3 is higher, subsequent levels such as Level 6, Level 7, . . . may be added in the same way. In this case, the additional levels are defined not to exceed the upper limit of the standard range; 320 cd/m². The permissible range (±20 cd/m²) at each level in the present embodiment is set as a range in which the background of optotypes is apparently unchanged. As an alternative, the permissible range at each level may be narrower (e.g. ±10 cd/m²) for finer change levels.

Figure 5:
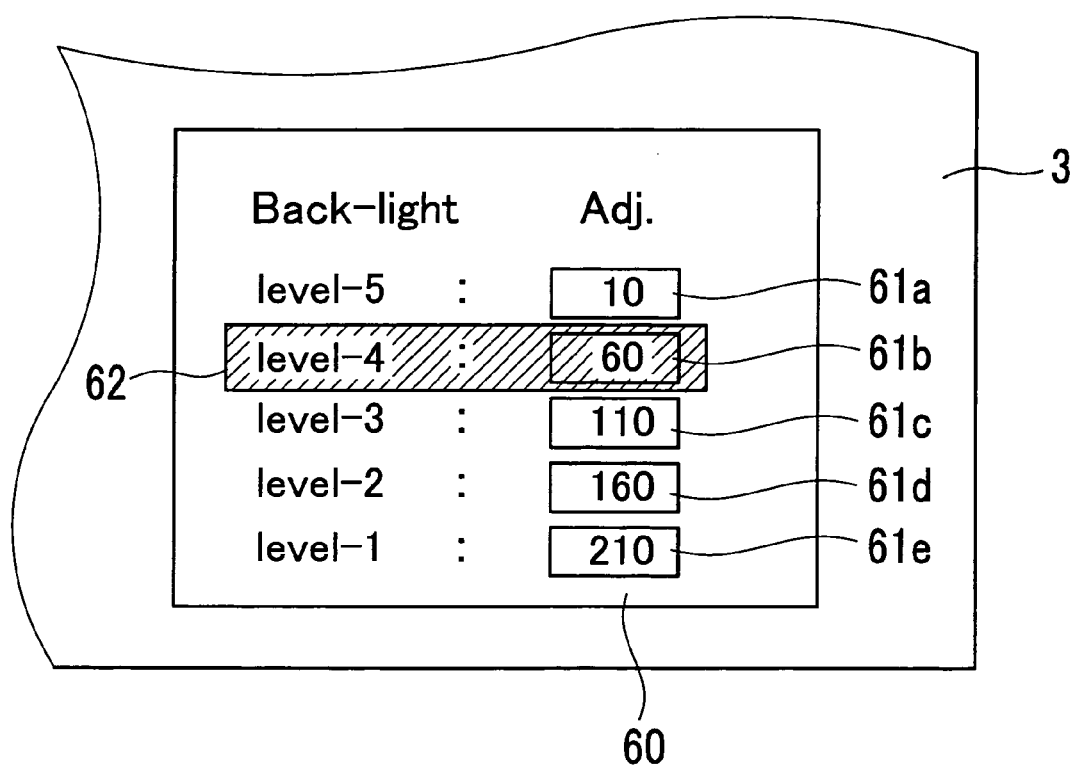
FIG. 5 is a view of an adjustment value setting screen.

A manner of setting the luminance adjustment value for each level is explained below. In a state where the test optotype 10 is displayed, when the switch 7e is pushed while the switch 7d is held pushed down, a luminance adjusting mode is established. An adjustment value setting section 60 shown in FIG. 5 appears in the lower right part of the screen of the display 3. Adjustment boxes 61a to 61e of the setting section 60 are used to enter adjustment values to be set as Levels 1 to 5. Initial adjustment values "10", "60", "110", "160", and "210" originally stored in the memory 21 are called up and displayed by the control unit 20. Each initial value is an average of the adjustment values to provide a target luminance at each level based on the luminance measurement results of many samples shown in FIG. 3.

The following explanation is given to an example in which the apparatus A shown in FIG. 4 is adjusted to set an luminance adjustment value for each level. When Level 4 is to be set, for example, a cursor 62 indicated by hatching in the figure is moved by the switch 7c onto an adjustment value box 61b. When the cursor 62 is moved in place, the control unit 20 calls up an initial value "60" for Level 4 from the memory 21 and applies a voltage corresponding to the adjustment value "60" to the backlight 3b of the display 3, thereby changing the intensity of the backlight 3b. An operator who adjusts the apparatus measures the luminance with a luminance meter. If the measured luminance is not close to a target luminance of 220 cd/m² at Level 4, the operator increases or decreases the adjustment value with the switch 7a or 7b. As the adjustment value in the box 61b is changed, the intensity of the backlight 3b is changed correspondingly. In the case of the apparatus A with higher luminance than average, the adjustment value is increased with the switch 7a to lower the luminance. It is experimentally found from the average of many apparatuses that the rate of change is about 10 cd/m² in steps of an adjustment value "10" as mentioned above. This may serve as a guide for changing the adjustment value. After changing the intensity of the backlight 3b and measuring the luminance with the luminance meter are repeated, the adjustment value corresponding to the target luminance at Level 4 is determined. As to the apparatus A, the adjustment value is set to "75", so that the luminance can be adjusted to about 220 cd/m² at Level 4.

As above, in each apparatus, the adjustment value corresponds to the luminance value. Accordingly, the following description mainly mentions increase and decrease in the adjustment value but may be read by replacing it with increase and decrease in the luminance value. This replacement also can embody the above concept.

After the adjustment value for Level 4 is set, the cursor 62 is moved to an adjustment value box 61c for Level 3. The adjustment value is changed in a similar manner to the above case to change the intensity of the backlight 3b. The luminance of the display 3 is then measured with the luminance meter. The adjustment value is set to achieve about a target luminance (180 cd/m²) for Level 3. The same manner is applied to Level 2, Level 1, and Level 5 to set respective adjustment values in boxes 61d, 61e, and 61a to achieve about respective target luminances. In the apparatus A, the adjustment values for Levels 1, 2, 3, 4, and 5 are set to for example "225", "175", "125", "75", and "25" respectively. Then, when the switches 7d and 7e are pressed together, the luminance adjusting mode is canceled and the screen of the display 3 is returned to the test optotype presenting state. Simultaneously, the initial values stored in the memory 21 are updated to the currently set adjustment values. It is to be noted that the standard luminance during manufacture is set as Level 4.

Further, an input device or means may be provided to directly input the luminance value measured by the luminance meter. In this case, it may be configured to compare the background luminance input by the input device or means and the target luminance and automatically calculate a correction adjustment value.

In other apparatuses B, C, D, and E, the luminance adjustment value corresponding to each level is set to be a specific value to each apparatus. In the apparatus E, the adjustment values for Levels 1, 2, 3, 4, and 5 are set to for example "200", "150", "100", "50", and "0" respectively. In FIG. 4, the parenthetic numerals in each bar graph indicating the adjustment range of each apparatus A to E are examples of an adjustment value corresponding to each level.

The luminances at Levels 1 to 5 can be set without falling outside the standard range in the above manner. However, it takes a lot of time and trouble to measure actual luminance at each level with the luminance meter and then adjust the luminance at each level so as to fall within the predetermined permissible range. The following explanation is given to an example of simplifying the adjustment work by executing an automatic luminance adjustment program previously stored in the memory 21.

An example of executing the automatic luminance adjustment program is explained. As with the aforementioned example, with simultaneous pressing of the switches 7d and 7e, the luminance adjusting mode is established and the control unit 20 executes the automatic adjustment program. The adjustment value setting section 60 is displayed in the lower right part of the display 3 as in FIG. 5. The initial values appear in the adjustment boxes 61a to 61e of the setting section 60. Herein, the program is configured so that when a certain value "X" is set as the adjustment value for Level 3, the adjustment values at other Levels 1, 2, 4, and 5 are automatically determined by the following calculation.

| | |
|---|---|
| Level 1: | X + 100 (Upper limit: adjustment value "255") |
| Level 2: | X + 50 |
| Level 3: | X |
| Level 4: | X − 50 |
| Level 5: | X − 100 (Lower limit: adjustment value "0") |

In each of the above levels, the numerals added to or subtracted from X are determined in view of that the luminance is nearly proportional to the adjustment value for the backlight 3b as shown in FIG. 3 and a rate of change is about 10 cd/m² in steps of an adjustment value "10".

In other words, when the adjustment value X for Level 3 is set to be about 180 cd/m² which is the center of the permissible range, the adjustment values at other Levels 1, 2, 4, and 5 are set by the above calculation to fall within respective permissible ranges.

A concrete explanation is given below. When the cursor 62 is moved to Level 3, the intensity of the backlight 3b is changed based on the initial adjustment value "110" for Level 3. The luminance is measured at this time with the luminance meter. The adjustment value is changed with the switch 7a or 7b to achieve a luminance of about 180 cd/m² which is the center of the permissible range. In the apparatus B of FIG. 4, for example, when the adjustment value for Level 3 is set to "118", thereby providing a luminance of about 180 cd/m², the adjustment values for Levels 1, 2, 4, and 5 are automatically set to "218"(118+100), "168"(118+50), "68"(118−50), and "18"(118−100), respectively. Then, the luminance adjusting mode is canceled with simultaneous pressing of the switches 7d and 7e and the adjustment values stored in the memory 21 are updated to the changed adjustment values. When the adjustment value for any one of Levels 1 to 5 is determined, the adjustment values for remaining levels are automatically set to provide the luminance in each permissible range. Thus, a simplified adjustment work can be achieved.

The above setting can reduce luminance differences among the apparatuses, thus enabling accurate tests. In an optician's shop or ophthalmological clinic, if the luminance is different between the existing optotype presenting apparatus used heretofore (e.g. a projecting type optotype presenting apparatus) and the newly adopted apparatus of the present embodiment, the luminance of the new apparatus is changed to have compatibility in test results with the apparatus used heretofore. To change the luminance, the switch 7b or 7a is pressed. Specifically, the luminance is changed stepwise up to the luminance at Level 1 with every press of the switch 7b and alternatively changed stepwise up to the luminance at Level 5 with every press of the switch 7a. Upon receipt of a luminance changing signal (a selection signal representing one of Levels 1 to 5) from the switch 7a or 7b, the control unit 20 calls up the adjustment value corresponding to the selected level and controls the voltage to be applied to the backlight 3b based on the adjustment value to change the luminance of the display 3. This luminance change to any one of Levels 1 to 5 may be decided by visually comparing the luminance with that of the existing apparatus. Even where the luminance is changed to the minimum luminance, Level 1, the luminance does not fall below 80 cd/m² which is the lower limit of the standard range. Even where the luminance is changed to the maximum luminance, Level 5, the luminance does not exceed 320 cd/m² which is the upper limit of the standard range. Accordingly, the luminance does not fall outside the standard range, thus enabling appropriate tests.

Figure 6:
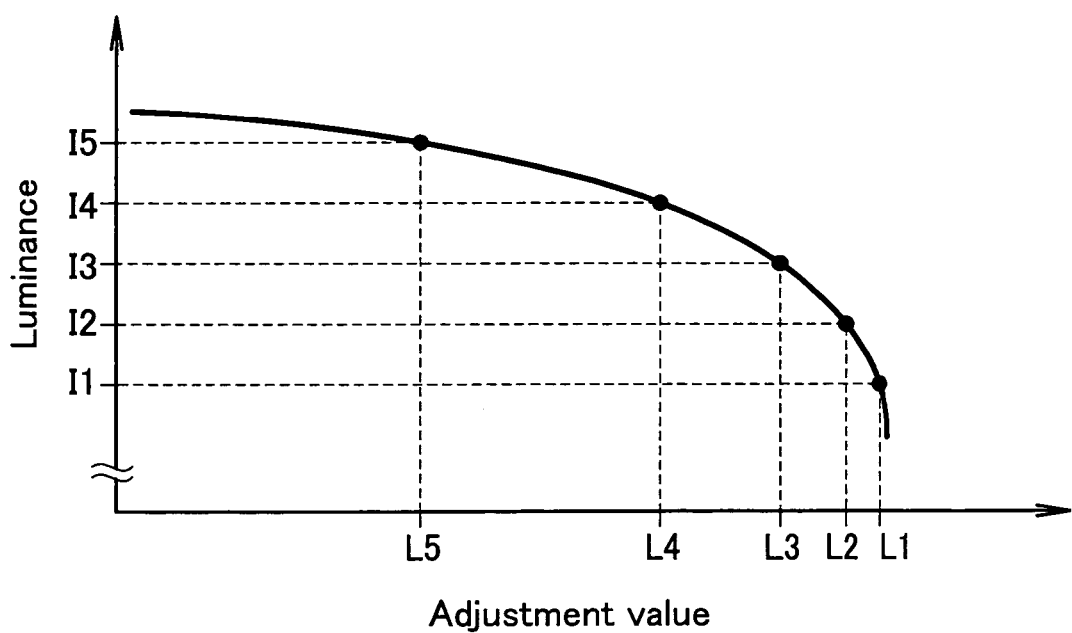
FIG. 6 is a graph showing a relationship between adjustment value and luminance in another configuration.

The rate of luminance change is nearly proportional to the change of adjustment value used in the luminance adjusting mode in the present embodiment. In some of the optotype presenting apparatuses, however, such almost proportional relationship could not always be provided depending on the characteristic of the backlight 3b of the display 3. It is for example conceivable that the luminance exhibits a parabolic curve with respect to the adjustment value as shown in FIG. 6. In this case, for example, the luminances corresponding to initial values L1, L2, L3, L4, and L5 for Levels 1 to 5 may be assumed to be I1, I2, I3, I4, and I5 respectively. Further, automatic setting may be adopted to add weight to the rate of change in the adjustment value by considering that the rate of change in each luminance I1 to I5 varies with respect to the change of the adjustment value around each of the initial values L1 to L5 for Levels 1 to 5.

In addition, the automatic setting in the luminance adjusting mode may be appropriately programmed according to the characteristic of the backlight 3b.

Even where a plurality of the apparatuses of the present embodiment is newly adopted and adjusted to change respective luminances to have compatibility with the existing apparatus(es), the luminances of the new apparatuses can be adjusted easily to be almost the same by setting the same one of Levels 1 to 5. In optician's chain of stores, when the luminances of the apparatuses in all the stores are adjusted to the same level, the luminance can be easily be changed to almost the same in all the stores, so that the apparatuses have compatibility to enable appropriate tests.

In the above explanation, the changeable range is defined by the standard range (80 to 320 cd/m²) permissible for the visual acuity test optotypes. However, some optician's shops may intentionally require lower or higher luminance than the standard range. To meet such requirement, the changeable levels may be increased in addition to at least the changeable levels corresponding to the standard range. In this case, preferably, a warning means is provided for example to cause the display 3 to show a message to inform that the luminance is changed to a level outside the standard range.

Figure 7:
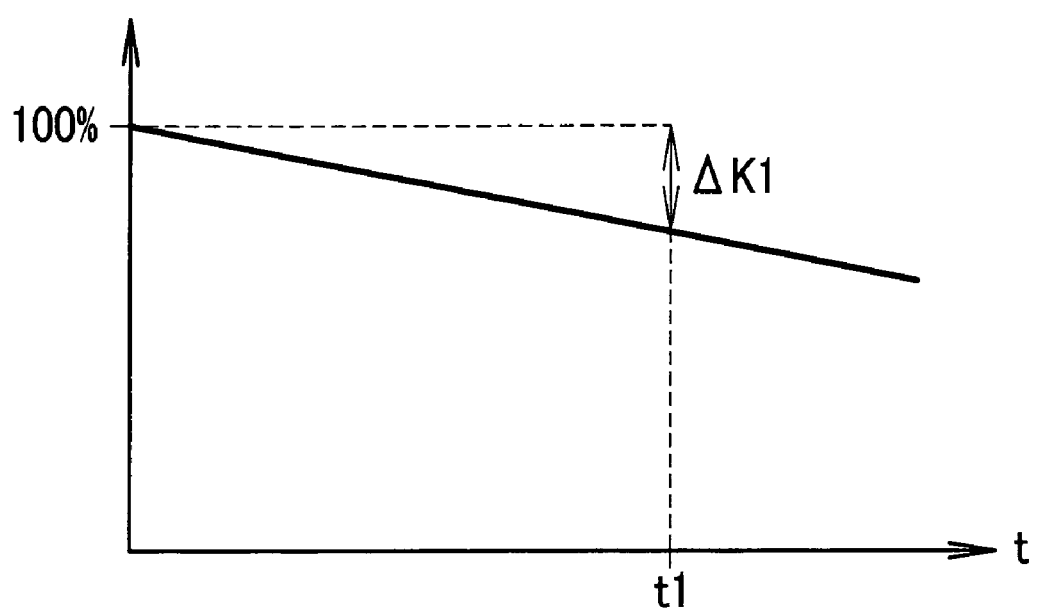
FIG. 7 is a graph to explain correction of decreased backlight intensity.

The following explanation is given referring to FIG. 7 to correction of decreased light intensity of the backlight 3b due to age deterioration. The display 3 is arranged to display the test optotype 10 and, in use for purposes other than tests, display graphics such as digital photographs under control of the control unit 20. In an optician's shop, the display 3 may be used for shop advertisement at any time other than tests. In this case, the backlight 3b is also turned on for other than tests and thus remains lighted for a long time. Accordingly, the backlight 3b of the display 3 is decreased in light intensity as the lighting time (operation time) is longer.

FIG. 7 is a graph to explain the rate of decrease in light intensity with respect to the lighting time "t" of the backlight 3b. The rate of decrease in light intensity to the lighting time is available from a manufacturer of the display 3 and also can be experimentally determined. A rate of decrease ΔK1 is the rate of decrease corresponding to a luminance decrease of 10 cd/m². The lighting time at that time is assumed to be t1. An arithmetic expression representing a relationship between this rate of decrease ΔK1 and the lighting time t1 is stored in advance in the control unit 20. The control unit 20 causes a timer 23 to measure the lighting time of the backlight 3b and, when the measured time reaches t1, the adjustment value corresponding to each level stored in the memory 21 is corrected based on the rate of decrease ΔK1. When the display 3 is used for a long period, the decrease in intensity of the backlight 3b is compensated. This makes it possible to maintain the luminance of the display 3 in a fixed range, thus enabling accurate tests.

The correction of decreased light intensity of the backlight 3b due to age deterioration may be performed automatically as above or manually. This manual correction is explained below. When the luminance of the display 3 appears to be lowered due to long use, a second luminance adjusting mode is established with press of the switches 7c and 7d, displaying an adjustment screen similar to that in FIG. 5 on the display 3. In this second luminance adjusting mode, when the adjustment value for any one (selected with the cursor 62) of the levels is changed to a desired one with the switch 7a or 7b, the control unit 20 uniformly changes the adjustment values for other levels by the same rate of change. For example, when the adjustment value for Level 4 is changed from "60" to "50", the adjustment values for other levels are also changed uniformly by the rate of change "−10". Then, the second luminance adjusting mode is terminated by pressing the switch 7a or 7b again. The adjustment values corresponding to the levels stored in the memory 21 are updated to the changed adjustment values. Accordingly, even the decrease in light intensity due to age deterioration can be supported easily.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optotype presenting apparatus which presents an optotype for visual acuity test, the apparatus comprising:
    a display that is illuminated by a backlight and includes a light intensity changing device which changes backlight intensity;
    a background luminance selecting device which selects background luminance of the optotype among a plurality of preset levels, in which background luminance at each level corresponds to standard light intensity changing data in a changeable range determined by the light intensity changing device; and
    a correction device which corrects the standard light intensity changing data in the background luminance selecting device, the correction device including:
        an input device which inputs the background luminance measured by an illuminance meter, the measured background luminance being background luminance obtained when the light intensity changing device is operated based on the preset light intensity changing data; and
        a calculation device which determines correction light intensity changing data by comparing the background luminance input by the input device and the preset light intensity changing data.

2. The optotype presenting apparatus according to claim 1, wherein
    the plurality of levels in the background luminance selecting device includes a minimum level that is close to and more than a lower limit of a standard range permissible for the visual acuity test optotype, a maximum level that is 200 cd/m$^2$ or higher and less than an upper limit of the standard range, and one or more middle levels defined between the minimum level and the maximum level.

3. The optotype presenting apparatus according to claim 1, wherein
    the calculation device of the correction device determines the correction light intensity changing data at each level based on the input background luminance and a light intensity change characteristic of the backlight.

4. The optotype presenting apparatus according to claim 3, wherein
    the calculation device calculates the light intensity change characteristic of the backlight by regarding a change in voltage applied to the backlight and light intensity of the backlight as being proportional to each other.

5. The optotype presenting apparatus according to claim 1, wherein
    the light intensity changing device includes a circuit for changing voltage to be applied to the backlight.

6. The optotype presenting apparatus according to claim 1, wherein
    the plurality of levels in the background luminance selecting device is determined to correspond to the standard light intensity changing data at the preset level in a stepwise changeable range from zero to a maximum value of the backlight of the display.

7. The optotype presenting apparatus according to claim 1, wherein
    a change in light intensity of the backlight due to age deterioration is stored, and
    the calculation device changes the correction light intensity changing data based on the age deterioration.

* * * * *